United States Patent [19]
Chen

[11] Patent Number: 5,866,736
[45] Date of Patent: Feb. 2, 1999

[54] PROCESS FOR THE PRODUCTION OF ALKYL BENZENE

[75] Inventor: Jamin Chen, Montville, N.J.

[73] Assignee: Catalytic Distillation Technologies, Pasadena, Tex.

[21] Appl. No.: 950,094

[22] Filed: Oct. 14, 1997

[51] Int. Cl.⁶ ................................................. C07C 2/66
[52] U.S. Cl. .................... 585/323; 585/446; 585/467; 585/470; 585/475
[58] Field of Search ................................. 585/323, 446, 585/467, 470, 475

[56] References Cited

U.S. PATENT DOCUMENTS

| | | | |
|---|---|---|---|
| 3,715,408 | 2/1973 | Brown et al. | 585/256 |
| 3,856,871 | 12/1974 | Haag et al. | 260/668 A |
| 3,948,758 | 4/1976 | Bonacci et al. | 208/92 |
| 3,957,621 | 5/1976 | Bonacci et al. | 208/60 |
| 4,007,231 | 2/1977 | Butter | 260/672 T |
| 4,038,334 | 7/1977 | Wood | 260/671 |
| 4,067,919 | 1/1978 | Butter | 260/668 D |
| 4,080,396 | 3/1978 | Butter | 260/673 |
| 4,101,595 | 7/1978 | Chen et al. | 260/668 A |
| 4,127,471 | 11/1978 | Suggitt et al. | 208/60 |
| 4,171,290 | 10/1979 | Mieville | 252/466 PT |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,250,052 | 2/1981 | Smith, Jr. | 252/426 |
| 4,302,356 | 11/1981 | Smith, Jr. | 252/426 |
| 4,307,254 | 12/1981 | Smith, Jr. | 568/697 |
| 4,319,067 | 3/1982 | Kreeger | 585/459 |
| 4,361,713 | 11/1982 | Kaeding | 585/467 |
| 4,443,559 | 4/1984 | Smith, Jr. | 502/527 |
| 4,721,827 | 1/1988 | Cullo et al. | 585/467 |
| 4,761,514 | 8/1988 | Menard | 585/475 |
| 4,849,569 | 7/1989 | Smith, Jr. | 585/446 |
| 4,891,458 | 1/1990 | Innes et al. | 585/323 |
| 4,975,179 | 12/1990 | Harandi et al. | 208/66 |
| 5,030,786 | 7/1991 | Shamshoum et al. | 585/467 |
| 5,198,595 | 3/1993 | Lee et al. | 585/467 |
| 5,240,892 | 8/1993 | Klocke | 502/77 |
| 5,243,116 | 9/1993 | Lee et al. | 585/467 |
| 5,464,799 | 11/1995 | Casci et al. | 502/65 |
| 5,476,978 | 12/1995 | Smith, Jr. et al. | 585/323 |

*Primary Examiner*—Walter D. Griffin
*Attorney, Agent, or Firm*—Kenneth H. Johnson

[57] ABSTRACT

The benzene content of light reformate is reduced by selectively alkylating the toluene contained therein with olefins by contacting the light reformate with the olefins in a catalyst bed. The catalyst structure in the catalyst bed acts as both a catalyst for the alkylation reaction and as distillation structure thus immediately separating the reaction product from the reaction zone to prevent reverse reactions and increase the overall reaction rate. The alkylated toluene is then used to transalkylate benzene to reduce the amount of benzene in the gasoline.

17 Claims, 2 Drawing Sheets

5,866,736

PROCESS FOR THE PRODUCTION OF ALKYL BENZENE

BACKGROUND OF THE INVENTION

The reduction in the lead content of gasolines and the use of lead anti-knock compounds has lead to a search for other ways to improve the octane number of blending components for gasoline. The alternatives to uses of lead anti-knock compounds are chemical processing and the use of other additives. Simultaneously with the reduction in lead has come the requirement that the benzene content of gasoline must be reduced.

One common process long used by the refinery industry to upgrade raw naphtha to high octane gasoline is catalytic reforming. In catalytic reforming the raw naphtha having a boiling range of circa 115°–350° F. is passed over an alumina supported noble metal catalyst at elevated temperatures (circa 920°–950° F.) and moderate pressure (circa 200–550 psig). The catalyst "reforms" the molecular structures of the hydrocarbons contained in the raw naphtha by removing hydrogen and rearranging the structure of the molecules so as to improve the octane number of the naphtha. However, the increase in octane number also reduces the liquid volume of the naphtha as the specific gravity is increased.

Because of the multiplicity of the compounds in the raw naphtha, the actual reactions which occur in catalytic reforming are numerous. However, some of the many resulting products are aryl or aromatic compounds, all of which exhibit high octane numbers. The aryl compounds produced depend upon the starting materials which in a refinery are controlled by the boiling range of the naphtha used and the crude oil source. One of the aryl compounds formed is benzene which as noted above is not desirable. One method suggested for reducing the benzene content of the reformate is to separate the benzene precursor (isohexane) from the feed to the catalytic reformer. See for example U.S. Pat. No. 4,975,179. This expedient, however, reduces the overall octane of the gasoline mixture.

The "reformed" product from a catalytic reforming process is commonly called reformate and is often separated into two fractions by conventional distillations—a light reformate having a boiling range of circa 115°–250° F. and a heavy reformate having a boiling range of circa 250°–350° F. The aryl compounds in each fraction are thus dependent upon their boiling points. The lower boiling or lighter aryl compounds, e.g., benzene, toluene and xylenes, are contained in the light reformate and higher boiling aryl compounds are contained in the heavy reformate.

A method of carrying out catalytic reactions has been developed wherein the components of the reaction system are concurrently separable by distillation using the catalyst structures as the distillation structures. Such systems are described variously in U.S. Pat. Nos. 4,215,011; 4,232,177; 4,242,530; 4,250,052; 4,302,356; and 4,307,254 commonly assigned herewith. Briefly, a structure described there is a cloth belt with a plurality of pockets spaced along the belt containing a particulate catalyst, which is then wound in a helix about a spacing material such as stainless steel knitted mesh. These units are then disposed in a distillation column reactor. In addition, commonly assigned U.S. Pat. No. 4,443,559 discloses a variety of catalyst structures for this use and is incorporated by reference herein.

It has been proposed to alkylate the aromatics, especially benzene, contained in a reformate stream utilizing the concurrent distillation/reaction method. See U.S. Pat. No. 5,082, 990. The direct alkylation of benzene with ethylene or propylene has been quite difficult due to fast catalyst deactivation. One reason for the fast deactivation is the requirement for high conversion of benzene. In the concurrent reaction/distillation the depletion of the benzene in the reaction mass increases the concentration of olefin around the catalyst leading to fast catalyst deactivation. In other types of reaction systems the coexistence of toluene and other aromatics leads to the production of a large amount of higher alkylated aromatics, depressing the vapor pressure of the reaction mixture. In addition the high non-aromatic $C_6$'s in the reformate make the alkylation of benzene more difficult. These hydrocarbons boil in about the same boiling range as benzene and are therefore difficult to separate from benzene without affecting the conversion of benzene.

However, there is almost three times as much toluene as benzene in the reformate and the alkylation of toluene with an olefin is relatively easy.

SUMMARY OF THE INVENTION

Briefly, the present invention is thus directed to selectively alkylating the toluene with an olefin and then transalkylating the resultant alkyl aromatic with benzene to obtain the corresponding alkyl benzene. If the purpose is to simply convert the benzene to the alkyl benzene then only about a stoichiometric amount of the toluene equivalent to the benzene to be alkylated in the alkylation step is present.

In one embodiment of the present invention the reformate and olefin are fed to a distillation column reactor containing a fixed bed acidic catalytic distillation structure in a feed zone. The $C_6$'s containing the benzene are taken overhead and the $C_7$'s are distilled down into a distillation reaction zone. The column is operated such that the toluene fraction is maintained in the reaction distillation zone for the desired conversion. The toluene catalytically reacts with the olefinic compounds to preferentially produce mono-substituted alkylated toluene compounds. At the same time, the alkylated toluene is fractionated from the unreacted materials in the fixed bed. The catalytic distillation structure provides both the catalytic sites and the distillation sites. The alkylated toluene is withdrawn from the distillation reactor at a point below the fixed bed and the unreacted materials are withdrawn overhead at a point above the fixed bed. Suitable acidic catalysts include molecular sieves (mole sieves).

The alkylated toluene is then fed along with the benzene to a transalkylation reactor which may be a single pass reactor containing a fixed bed of the same catalyst used in the distillation column. The alkyl toluene transalkylates benzene to the corresponding alkyl benzene while the alkyl toluene is converted back to toluene.

More specifically the acid catalyst, e.g., mole sieve catalyst packing is of such a nature as to allow vapor flow through the bed, yet provide a sufficient surface area for catalytic contact as described in the previously noted U.S. Pat. Nos. 4,443,559; 4,215,011 and 4,302,356 which are incorporated herein in their entirety. The catalyst packing is preferably arranged in the middle portion of the distillation column reactor.

DETAILED DESCRIPTION OF THE INVENTION

Figure 1:
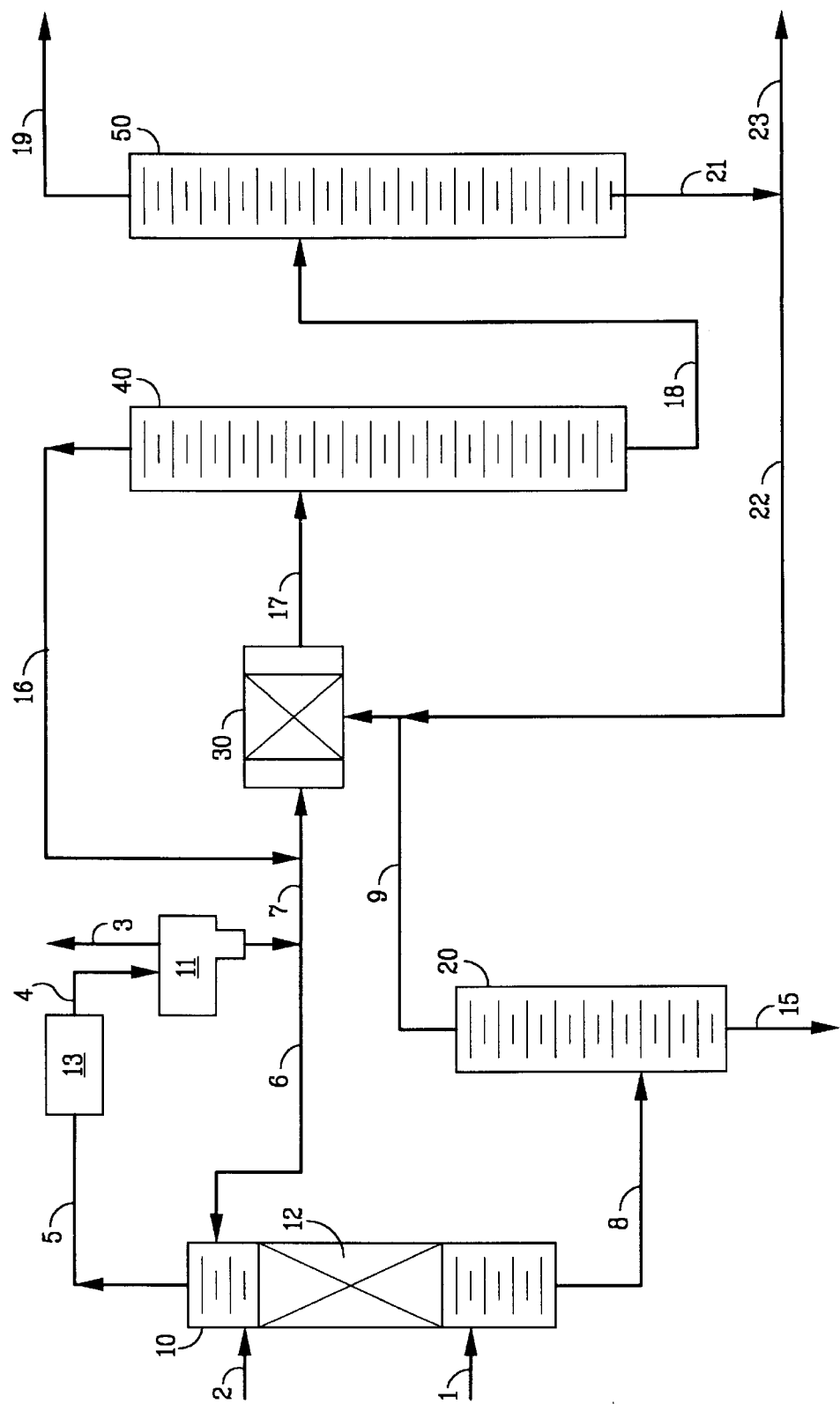
FIG. 1 is a schematic representation of a preferred embodiment of the present invention using a single column reactor splitter.

The process of the present invention relates to reducing the benzene content of the light reformate by combining the light reformate with an olefin to produce an alkyl aromatic product. The olefin can be contained in an otherwise "waste gas" stream from another common refinery processing unit—a fluid catalytic cracking unit or FCCU. In fluid catalytic cracking a heavy "gas oil" stream having a boiling range circa 600°–900° F. is combined with a fine catalytic substance, usually a zeolitic material, at elevated temperatures, about 900° F., which breaks apart or cracks the longer chain hydrocarbons to shorter chain hydrocarbons. In the absence of hydrogen (and suitable hydrogenation pressures) some unsaturated compounds are produced. Some gas is produced, the amount depending on the severity of the cracking, the gas also being rich in unsaturated compounds, i.e., ethylene, propenes, and butenes. Since the compounds have value, they are usually recovered and used or sold separately. However, the unsaturated compound or olefin separation results in "waste gas" having an olefin content of up to 10 mole percent. This waste gas is normally used as fuel in the refinery heaters.

The olefin is preferably a lower olefin, i.e., a $C_2$ to $C_4$ mono-olefin which may be in a high purity form or a component of a waste gas. Also the olefin may be a mixture of lower olefins.

A particularly unexpected benefit of the use of the process centers on the combined reaction distillation going on in the column. The reformate comprises a mixture of organic aromatic compounds boiling over a range. The product from the alkylation can be tailored by adjusting the temperature in the column to fractionate the reformate feed concurrently with the reaction of olefin and aromatic compound and the distillation of the alkylated product. Any cut can be made that is within the capacity of the equipment. The light end of the reformate can be taken overhead, heavies taken as bottoms and a high concentration of toluene maintained in the portion of the column containing the catalytic distillation structure. Thus the alkylation is primarily carried out with the toluene to produce an alkyl toluene for transalkylation of the benzene. Any excess alkyl toluene is a gasoline component of desirable properties which can then be recombined with the other components of the reformate. This is not possible with a straight pass alkylation of the same components where the resulting product would not be a discernible improvement because there is an indiscriminate alkylation of the aromatic components in the reformate and olefin conversion would have to be kept very low because of the heat of reaction and polymerization of high concentration of olefins.

The alkylated product is the highest boiling material and is separated in the lower portion of the column usually as bottoms. The light reformate is the second highest boiling component. The success of catalytic distillation lies in an understanding of the principles associated with distillation. First, because the reaction is occurring concurrently with distillation, the initial reaction product is removed from the reaction zone as quickly as it is formed. The removal of the alkylation product minimizes polysubstitution, decomposition of the alkylation product and/or oligomerization of the olefinic compounds. Second, because the light reformate is boiling, the temperature of the reaction is controlled by the boiling point of that component at the system pressure. The heat of the reaction simply creates more boil up, but no increase in temperature. The reaction has an increased driving force because the reaction products have been removed and cannot contribute to a reverse reaction (Le Chateliers's Principle).

As a result, a great deal of control over the rate of reaction and distribution of products can be achieved by regulating pressure. Also the through-put (residence time=liquid hourly space velocity$^{-1}$) gives further control of product distribution and degree of olefin conversion.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa.

It can also be appreciated that in catalytic distillation as in any distillation there is both a liquid phase (internal reflux) and a vapor phase. Thus, the reactants are partially in liquid phase which allows for a low concentration of olefins in the reacting liquid, whereas, the concurrent fractionation separates product and unreacted materials, providing the benefits of a liquid phase system (and a vapor phase system) while avoiding the detriment of having all of the components of the reaction system continually in contact with the catalyst. High concentrations of olefin cause catalyst deactivation by polymerization and polysubstitution reactions.

An FCCU waste gas, if used as the olefin, contains a variety of unrecovered olefins, however the preponderant olefinic compounds are ethylene, propylene (propenes) and butenes. The remainder of the gas is made up of various saturated hydrocarbons. Table I below gives an analysis of a typical waste gas used in the invention. The analysis was performed by gas chromatography and the components are given as weight percent.

TABLE I

Typical Gas Analysis

| Component | wt. % |
|---|---|
| $C_1$ | 21.1 |
| $C_2=$ | 11.1 |
| $C_2$ | 12.7 |
| $C_3=$ | 30.6 |
| $C_3$ | 7.9 |
| $C_4=$ | 0.4 |
| $C_4$ | 0.7 |
| $C_5+$ | 0.1 |
| $N_2$ | 13.5 |
| $H_2$ | 1.7 |
| $CO_2$ | 0.3 |

As may be seen from the analysis of the waste gas the typical total olefin content is 42.1 percent, divided into ethylene, 11.1 percent; propene, 30.6 percent; and butenes and higher, 0.4 percent.

A typical light reformate with a research octane number of 87.4 and an ASTM boiling range of 152° to 239° F. has an analysis as shown in Table II.

TABLE II

Typical Light Reformate Analysis

| Component | wt. % |
|---|---|
| $C_3$ to $C_8$ non aromatics | 55.5 |
| Benzene | 9.5 |
| Toluene | 32.5 |
| Ethylbenzene + Xylenes | 2.0 |
| $C_9$ aromatics | 0.2 |
| $C_{10}$ aromatics | 0.2 |
| $C_{11}$ aromatics | 0.2 |

While it will be appreciated that the light reformate analysis is dependent upon the composition of the raw naphtha, all light reformates contain some of the aryl compounds shown above to a greater or lesser extent.

In any case the olefinic compounds whether fed as a relatively pure stream or contained in the waste gas will always have a lower boiling point that the light reformate.

In a particular embodiment which is of current commercial importance ethylene or propylene is reacted with toluene in the light reformate according to the present invention to form methyl ethyl benzene or methyl propyl benzene, respectively. In both of these reactions the olefin is the most volatile component and it is desirable to react it rather than have some carried off overhead. Benzene is taken as overheads and the alkylated toluene is taken as bottoms along with any other heavy compounds in the reformate. The alkylated toluene is then separated from the other heavy material for feed to the transalkylation reactor.

The length of the catalyst bed, particularly that portion wherein the reactants are in contact and the major portion of the reaction occurs, depends on the reactants, location of the olefin feed and the acceptable unreacted olefin in the streams leaving the tower. Some degree of development testing will be required for each set of reactants (as determined by crude source of the raw naphtha and the waste gas composition) and parameters of stream purity following present disclosures.

The present alkylation reaction can be carried out at sub-through super atmospheric pressure, e.g., 0.20 to 40 atmospheres. The temperature will vary depending on the reactants and product. Furthermore, the temperature along the column will be as in any distillation column; the highest temperature will be in the bottom and the temperature along the column will be the boiling point of the compositions at that point in the column under the particular conditions of pressure. Moreover, the exothermic heat of reaction does not change the temperature in the column but merely causes more boil up. However, the temperatures within the column with the above considerations in mind will generally be in the range of 70° C. to 500° C. for the mole sieve and 70° C. to 150° C. for the cation exchange resin, and more preferably in the range of about 80° C. to 300° C. at pressures of 0.5 to 50 atmospheres for the mole sieve and about 80° C. to 150° C. at 0.25 to 10 atmospheres for the resin catalyst.

The transalkylation reactor can utilize the same catalyst as in the distillation column reactor. However, the reactor is preferably a standard straight pass type reactor, preferably in liquid phase. The alkyl toluene and benzene can be fed to the transalkylator in a 1:1 mole ratio or with an excess of alkyl toluene. Any excess alkyl toluene can be recycled to the transalkylator or used as a gasoline blending component. The pressure in the transalkylator can be from 50 to 600 psig and the temperature can be from 300° to 500° F.

The preferred olefins for the process are either ethylene or propylene which may be fed as a substantially pure stream or in the FCCU waste gas. The resultant products for ethylene are methyl ethyl benzene as the alkyl toluene and ethyl benzene for the alkyl benzene. The resultant products for propylene are methyl propyl benzene for the alkyl toluene and cumene for the alkyl benzene.

Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., insofar as the natural zeolites are the functional equivalents to the synthetic zeolites.

Usually synthetic zeolites are prepared in the sodium form, that is, with a sodium cation in close proximity to each aluminum tetrahedron and balancing its charge. To date four principal types of molecular sieves have been reported, A, X, Y and L erionite, omega, beta and mordenite. The A type have relative small pore size. By the term pore size is meant the effective pore size (diameter) rather than the free pore size (diameter). Types X and Y have larger pore size (approximately 10 Å.) and differ as to the range of ratio of $Al_2O_3$ to $SiO_2$ as:

Type X—$Al_2O_3/2.0$–3.0 $SiO_2$
Type Y—$Al_2O_3/3.0$–6.0 $SiO_2$
Type L, beta and other types listed have still higher ratios of $SiO_2$ to $Al_2O_3$.

The mole sieve catalysts employed in the present invention are the acid form mole sieves or exhibit acidic characteristics. The acid form of the mole sieves is commercially available but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with soluble ammonium salts to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability.

In addition to mole sieves which are acidic according to the Bronsted Theory, those mole sieves which exhibit acidic characteristics under the Lewis Theory, for example, calcium exchanged mole sieves are suitable for the present reaction. By exchanging the univalent cations (e.g. $Na^+$) with multivalent cation, strong ionic activity is imparted. The ratio of $SiO_2:Al_2O_3$, valence and radius of the cation and the extent of exchange all affect the catalyst activity. In general, activity increases with (1) increased $SiO_2:Al_2O_3$ ratio, (2) decreased cation radius and an increase in cation valence. The effect of replacing univalent ions (e.g. Na⁺) with bivalent (e.g. Ca⁺⁺) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal. The acid form mole sieves are generally produced and available as particles in the range of <10 micron (powders) to 0.2 inch in diameter (beads).

In this form the mole sieves form too compact a bed and will not function adequately in a distillation since there is a very large pressure drop through the bed and the free flow of internal reflux and rising vapor is impeded. Mole sieves in the shape of conventional distillation structures, such as rings, saddles, and the like may be used in the present invention. The particulate mole sieves may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus, desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like, each such larger component may be individually intimately associated with or surrounded by the spacing component as described above.

It is not essential that the spacing component entirely cover the catalyst component. It is only necessary that the spacing component, intimately associated with the catalyst component, will act to space the various catalyst components away from one another as described above. Thus, the spacing component provides in effect a matrix of substantially open space in which the catalyst components are randomly but substantially evenly distributed.

A preferred catalytic distillation structure for use herein comprises placing particulate catalyst, e.g., the mole sieve particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred.

In the following examples the catalyst packing consists of bags in the form of a fiber glass cloth belt approximately six inches wide with narrow pockets approximately ¾ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles, which otherwise form a very compact bed which has a high pressure drop. Thus, the down flowing liquid is in intimate contact with the rising vapors in the column.

In commercial-scale operations, it is contemplated, catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing could be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

Referring now to FIG. 1, a generalized flow diagram is pictured. The distillation column reactor is depicted at 10 with the upper and lower quarters of the column filled with standard distillation structure, e.g., packing or trays. The middle half of the column is filled with the catalytic distillation structure as packing indicated at 12. The light reformate feed is fed into the column above the catalytic reaction zone 12 via line 2. The olefin is fed into the column below the catalytic reaction zone 12 via line 1. The olefin reacts with the toluene in the light reformate in the reaction zone to form higher boiling alkylated toluene which is distilled off the catalyst into the lower distillation section. Any unreacted light reformate and olefin which might be carried downward are boiled back up into the reaction zone for further reaction, while the alkylated product exits the bottom of the column through line 8. Generally the unreacted lighter components containing the benzene are taken overhead through line 5 to condenser 13 where the unreacted light reformate is condensed. The combined unreacted products (gas and reformate) are then passed to accumulator 11 through line 4 where the gasses are allowed to become separated from the liquid reformate. The unreacted gasses are taken out the top of the accumulator via line 3 and the liquid light reformate taken out where it may be sent back to the distillation column as reflux via line 6 to the reaction zone or fed to the transalkylator 30 via line 7.

The bottoms in line 8 are fed to a distillation column 20 where the alkyl toluene is separated from the other heavies. The heavies are removed from the distillation column 20 via line 15 and may be sent to gasoline blending. The alkyl toluene is taken overhead and fed to the transalkylator 30 via line 9. In the transalkylator 30 the benzene is transalkylated by the alkyl toluene to the corresponding alkyl benzene. The product from the transalkylator is taken via line 17 to a second distillation column 40 where the unreacted benzene is separated from the product and recycled to transalkylator 30 via line 16. The alkyl benzene is taken as bottoms along with unreacted alkyl toluene and toluene via line 18 and fed to a third distillation column 50. The alkyl benzene and toluene are taken as overheads via line 19 and the unreacted alkyl toluene is taken as bottoms via line 21 for recycle to transalkylator via line 22 or for gasoline blending via line 23.

Such conventional items as valves, reboilers, slip streams, etc. are not shown, but would be obvious expedients to those setting up such equipment.

In one embodiment of the invention, the light reformate may be fed to the accumulator and thus to the reaction zone with the reflux.

Figure 2:
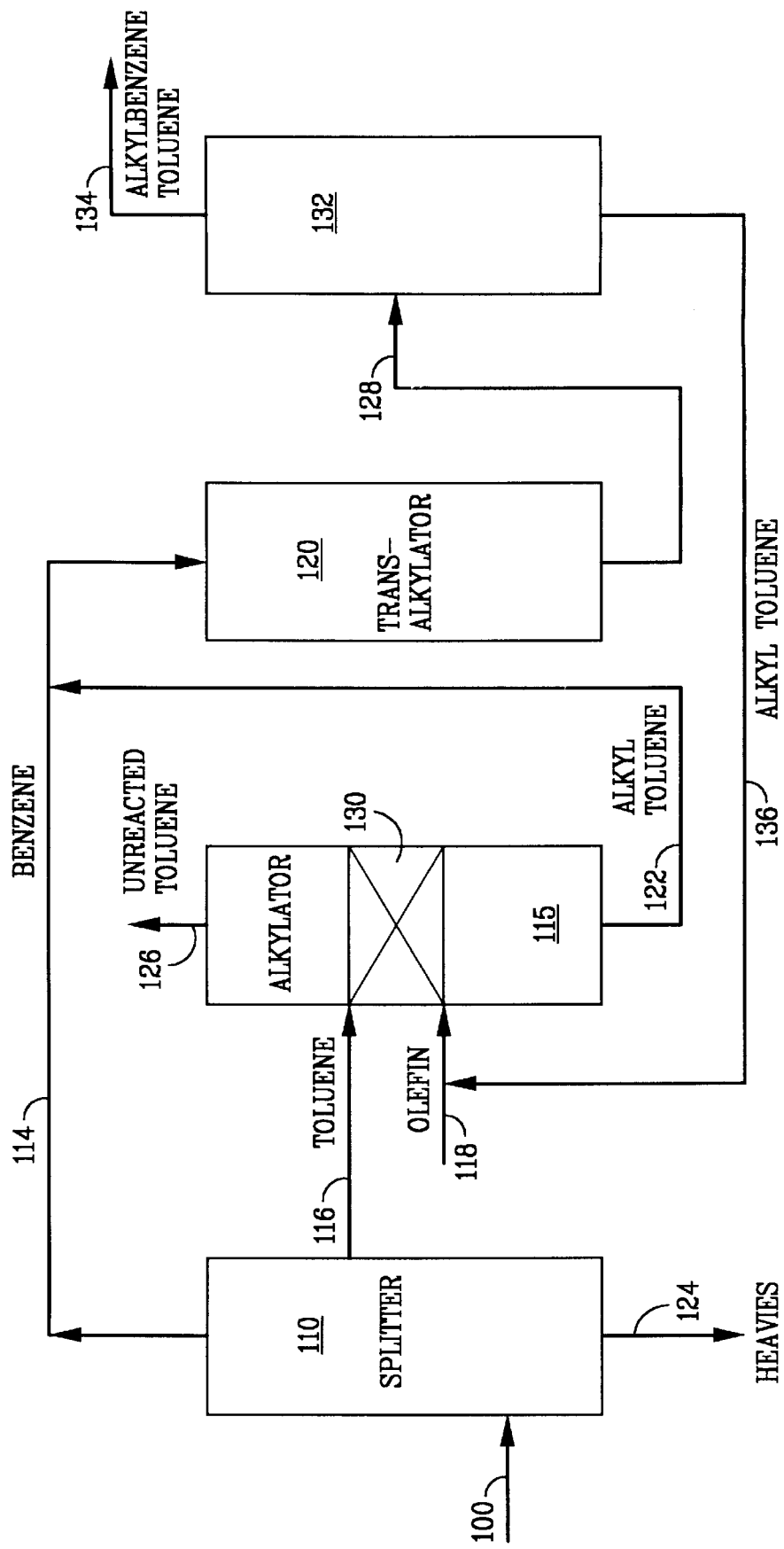
FIG. 2 is a schematic representation of an embodiment with a splitter before the reactor.

FIG. 2 shows a splitter 110 which receives the reformate feed 100. The reformate is fractionated to remove heavies out as bottoms 124 and benzene as overhead 114. The benzene goes to transalkylator 120 where it contacts alkyl toluene with an appropriate catalyst to produce product 128 which is primarily alkyl benzene and toluene which can be safely blended into gasoline.

This embodiment has the advantage that the heavies are removed before alkylator 112. Hence, the unit 112 can be much smaller. Additionally, the heavies do not contact the catalyst and there is less fouling. The toluene is removed from splitter 110 with a side draw 116 and preferably feed to alkylator 115 above the catalyst bed 130 which is described above for FIG. 1.

Usually $C_2$–$C_4$ olefin is fed below the catalyst bed 130 and rises to meet the heavier toluene. The alkylation need only proceed to the extent necessary to provide a stoichiometric or somewhat excess of the alkyl toluene to transalkylate with the benzene in transalkylator 120.

The alkyl toluene is the heaviest material in the alkylator 115 and passes as bottoms 122 to the transalkylator for concurrent flow with the benzene operated at sufficient pressure to maintain at least a partial liquid phase. If a stoichiometric excess of alkyl toluene is fed to transalylator 120, there will be an unreacted amount that can be recycled.

The product 128 from the transalkylator is fractionated for example in a splitter 132 and the lighter toluene and ethyl benzene recovered overhead 134 while the excess alkyl toluene is recycled through the alkylator. The excess alkyl toluene may be used as a diluent of the olefin.

The invention claimed is:

1. A process for producing alkyl benzene from the benzene contained in light reformate from a catalytic reforming unit, comprising:
   (a) feeding a light reformate stream containing benzene and toluene to a distillation column reactor into a feed zone;
   (b) feeding a gas stream containing olefins into said feed zone;
   (c) concurrently:
       (1) withdrawing benzene from the distillation column reactor from said light reformate at a point above a reaction zone
       (2) contacting the remainder of said light reformate stream having a substantially reduced benzene content from said light reformate and said gas stream with a fixed bed acidic catalytic distillation structure in said distillation reaction zone thereby catalytically reacting at least a portion of said toluene with said olefins to form alkyl toluene;
       (3) fractionating the resultant alkyl toluene from unreacted material; and
       (4) withdrawing the alkyl toluene from the distillation column reactor at a point below said reaction zone; and
   (d) feeding said benzene and alkyl toluene to a transalkylator containing an acidic catalyst wherein a portion of said benzene is transalkylated to alkyl benzene.

2. The process of claim 1 wherein said olefin is contained in an FCCU off gas stream.

3. The process of claim 1 wherein said catalysts are Y-molecular sieve, omega-molecular sieve or beta-molecular sieve.

4. The process of claim 1 wherein said light reformate is fractionated in said distillation column reactor to maintain toluene in the distillation reaction zone to selectively react a portion of said toluene with the olefinic compounds to form alkyl toluene.

5. The process according to claim 4 wherein only a portion of said alkyl toluene is fed to said transalkylator.

6. The process according to claim 1 wherein said distillation column reactor is operated such that the molar conversion of the toluene to alkyl toluene is equal to the molar concentration of benzene in said light reformate.

7. A process for producing alkyl benzene from the benzene contained in light reformate from a catalytic reforming unit, comprising:
   (a) feeding a light reformate stream containing benzene and toluene to a distillation column reactor into a feed zone;
   (b) feeding a gas stream containing olefins into said feed zone;
   (c) concurrently:
       (1) contacting said light reformate stream and said gas stream with a fixed bed acidic distillation structure comprising a mole sieve in a distillation reaction zone thereby catalytically reacting at least a portion of said toluene with said olefins to form a reaction mixture containing alkyl toluene; and
       (2) fractionating said reaction mixture to:
           (i) maintain the toluene contained in said light reformate in the distillation reaction zone to selectively react substantially all of said toluene with the olefinic compounds to form alkyl toluene, and
           (ii) separate the resultant alkyl toluene from unreacted material;

(3) withdrawing the alkyl toluene from the distillation column reactor at a point below said reaction zone;

(4) withdrawing benzene from the distillation column reactor at a point above said reaction zone;

(d) feeding said benzene and alkyl toluene to a transalkylator containing an acidic catalyst wherein a portion of said benzene is transalkylated to alkyl benzene; and (e) separating said alkyl benzene from unreacted benzene and unreacted alkyl toluene by fractional distillation.

8. The process according to claim 7 wherein a portion of said unreacted alkyl toluene is recycled to said transalkylator.

9. The process according to claim 7 wherein said unreacted benzene is recycled to said transalkylator.

10. The process according to claim 7 wherein said olefin comprises ethylene, said alkyl toluene comprises methyl ethyl benzene and said alkyl benzene comprises ethyl benzene.

11. The process according to claim 7 wherein said olefin comprises propylene, said alkyl toluene comprises methyl propyl benzene and said alkyl benzene comprises cumene.

12. A process for producing alkyl benzene from the benzene contained in light reformate from a catalytic reforming unit, comprising:

(a) feeding a light reformate stream containing benzene and toluene to a distillation column reactor into a first feed zone;

(b) feeding a gas stream containing olefins into said second feed zone;

(c) concurrently:
(1) contacting said light reformate stream and said gas stream with a fixed bed acidic catalytic distillation structure in a distillation reaction zone thereby catalytically reacting at least a portion of said toluene with said olefins to form a reaction mixture containing alkyl toluene; and (2) fractionating said reaction mixture to:
(i) maintain the toluene contained in said light reformate in the distillation reaction zone to selectively react substantially a molar amount of said toluene equal to the molar concentration of benzene in said light reformate with the olefinic compounds to form alkyl toluene, and (ii) separate the resultant alkyl toluene from unreacted material;

(3) withdrawing the alkyl toluene from the distillation column reactor at a point below said reaction zone;

(4) withdrawing benzene from the distillation column reactor at a point above said reaction zone;

(d) feeding said benzene and alkyl toluene to a transalkylator containing an acidic catalyst wherein a portion said of benzene is transalkylated to alkyl benzene; and (e) separating said alkyl benzene from unreacted benzene by fractional distillation.

13. The process according to claim 12 wherein said first feed zone is located above said distillation reaction zone.

14. The process according to claim 13 wherein said second feed zone is located within or below said distillation reaction zone.

15. A process for producing alkyl benzene from benzene contained in light reformate comprising:

(a) separating a portion of said benzene from said light reformate to produce a benzene deficient light reformate.

(b) concurrently:
(1) feeding said benzene deficient light reformate to a distillation column reactor containing a distillation structure comprising an acid catalyst comprising a mole sieve in a reaction zone;

(2) feed a lower olefin to said distillation column reactor;

(3) contacting the toluene in said benzene deficient light reformate and said lower olefin with said catalyst to form a reaction mixture comprising alkyl benzene;

(4) fractionating said reaction mixture;

(5) recovering alkyl toluene at a point below said reaction zone;

(6) recovering unreacted material above said reaction zone;

(c) feeding said benzene and said alkyl toluene to a transalkylator containing a fixed bed acidic catalyst comprising mole sieve to contact said catalyst and produce alkyl benzene and toluene.

16. The process according to claim 15 wherein said benzene and alkyl toluene are at least in partial liquid phase in said transalkylator.

17. The process according to claim 16 wherein said benzene and alkyl toluene are maintained in liquid phase.

\* \* \* \* \*